US012268465B2

(12) United States Patent
Corbeil et al.

(10) Patent No.: US 12,268,465 B2
(45) Date of Patent: Apr. 8, 2025

(54) DISPLACEMENT MECHANISM FOR PATIENT CONTROLLED PLACEMENT AND REMOVAL OF AN OPTICAL DEVICE IN A CONFINED SPACE ENVIRONMENT

(71) Applicant: Siemens Medical Solutions USA, Inc., Malvern, PA (US)

(72) Inventors: James L. Corbeil, Knoxville, TN (US); Martin Judenhofer, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 275 days.

(21) Appl. No.: 17/457,334

(22) Filed: Dec. 2, 2021

(65) Prior Publication Data
US 2023/0172452 A1 Jun. 8, 2023

(51) Int. Cl.
A61B 5/00 (2006.01)
A61B 5/055 (2006.01)
A61B 6/00 (2024.01)
A61B 6/03 (2006.01)
B25J 1/12 (2006.01)

(52) U.S. Cl.
CPC ............ A61B 5/0035 (2013.01); A61B 5/055 (2013.01); A61B 6/037 (2013.01); A61B 6/5247 (2013.01); B25J 1/12 (2013.01)

(58) Field of Classification Search
CPC ........................................................ B25J 1/12
See application file for complete search history.

(56) References Cited

U.S. PATENT DOCUMENTS

| 2004/0220467 A1* | 11/2004 | Bonutti | A61B 6/0421 600/407 |
| 2006/0251312 A1 | 11/2006 | Krieg et al. | |
| 2008/0156993 A1 | 7/2008 | Weinberg et al. | |
| 2008/0269594 A1 | 10/2008 | Paul et al. | |
| 2009/0093705 A1 | 4/2009 | Vangdal | |
| 2015/0096570 A1* | 4/2015 | Noras | A61B 5/6814 128/869 |

(Continued)

OTHER PUBLICATIONS

International application No. PCT/US2020/070162, filed Jun. 22, 2020, entitled Digital Display for a Medical Imaging System Bore, Applicant file reference, Applicant Siemens Medical Solutions USA, Inc. (copies of specification, claims, abstract, and PCT Notice attached).

Primary Examiner — Serkan Akar

(57) ABSTRACT

A displacement mechanism for placing an optical device onto a patient's eyes and removing the optical device from the patient's eyes when the patient is located in a patient bore of a medical imaging system. The mechanism includes a pneumatic device and a resilient element attached between an inner surface of the patient bore and the optical device wherein the resilient element extends through the pneumatic device and wherein the optical device is spaced apart from the patient's eyes in a first position. A pump inflates the pneumatic device to move the optical device to a second position wherein the optical device is placed on the patient's eyes. Inflation of the pneumatic device extends the resilient element and biases the resilient element to return to the first position. A vent valve vents air from the pneumatic device to return the optical device to the first position.

13 Claims, 4 Drawing Sheets

(56) References Cited

U.S. PATENT DOCUMENTS

| | | |
|---|---|---|
| 2015/0097756 A1 | 4/2015 | Ziarati et al. |
| 2016/0051187 A1 | 2/2016 | Damadian |
| 2016/0206848 A1 | 7/2016 | Glenn |
| 2016/0213301 A1 | 7/2016 | Port |
| 2018/0197337 A1 | 7/2018 | Forthmann et al. |
| 2019/0101243 A1 | 4/2019 | Zou et al. |
| 2019/0366030 A1 | 12/2019 | Giap et al. |
| 2020/0029880 A1 | 1/2020 | Katnani et al. |
| 2021/0106300 A1 | 4/2021 | Bal et al. |
| 2021/0166662 A1 | 6/2021 | Wang et al. |
| 2021/0274152 A1 | 9/2021 | Ziarati et al. |
| 2022/0280041 A1* | 9/2022 | Goertzen ............... A61B 5/704 |

* cited by examiner

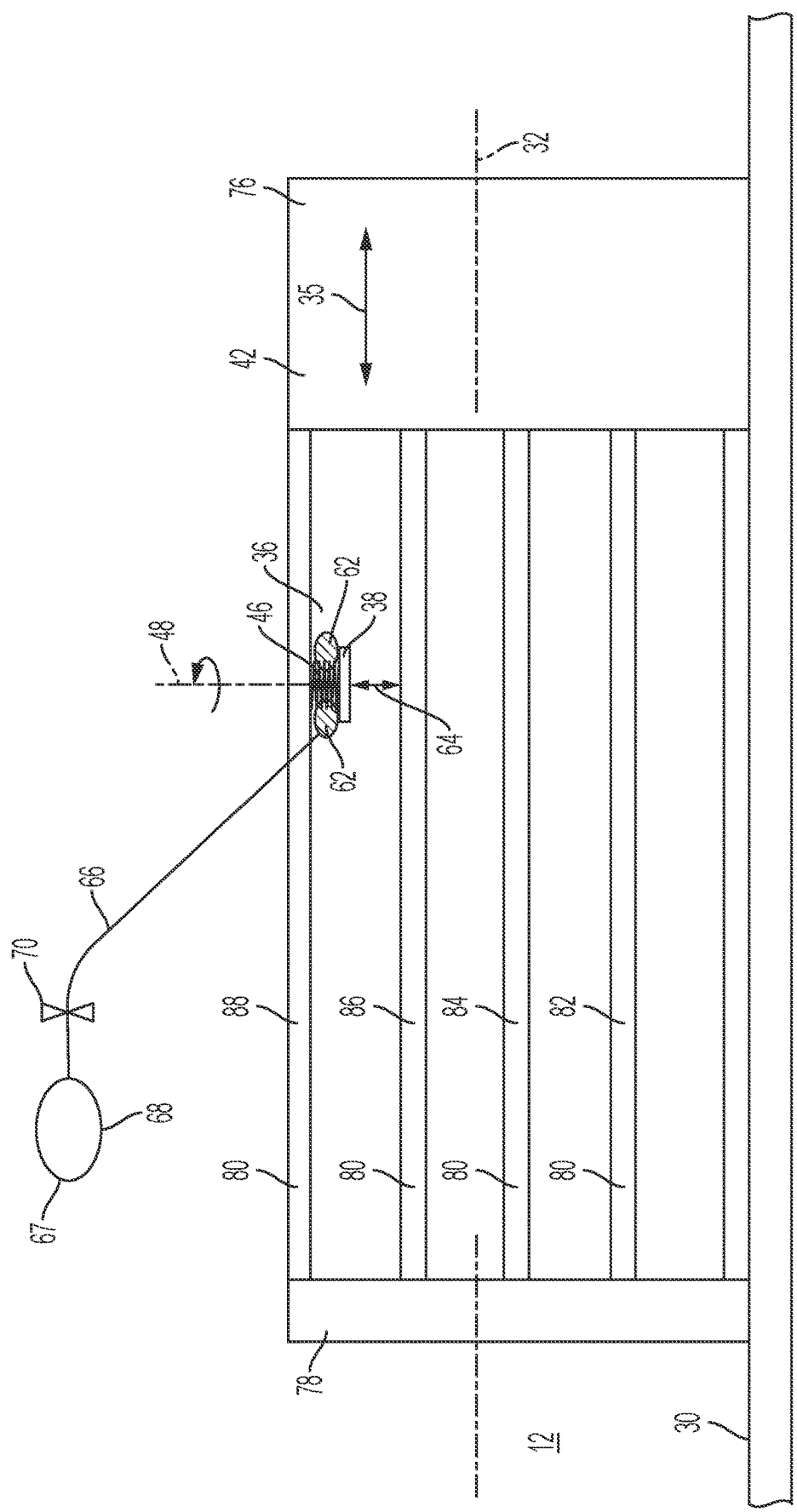

DISPLACEMENT MECHANISM FOR PATIENT CONTROLLED PLACEMENT AND REMOVAL OF AN OPTICAL DEVICE IN A CONFINED SPACE ENVIRONMENT

TECHNICAL FIELD

Aspects of the present invention relate to a displacement mechanism for controlling placement and removal of an optical device, and more particularly, to a displacement mechanism that includes a pneumatic device and a resilient element wherein in a first position the optical device is spaced apart from the patient's eyes and when the pneumatic device is inflated the optical device moves to a second position wherein the optical device is placed on the patient's eyes and wherein inflating the pneumatic device biases the resilient element to return to the first position and venting the pneumatic device returns the optical device to the first position.

BACKGROUND

Many medical imaging systems include an imaging bore that receives a patient, or a test subject participating in research, who is to be imaged or scanned. The bore is typically elongated and forms a tunnel that may be imposing or intimidating to those that are either young or for adults who suffer from claustrophobia or other conditions. In a type of imaging system known as a magnetic resonance/positron emission tomography (MR/PET) imaging system, components from MR and PET imaging systems are integrated to form a single hybrid imaging system having two different imaging modalities. With respect to MR and PET/MR imaging systems that operate at relatively at high magnetic field strengths, the configuration of components such as the magnet, gradient coil, radio frequency (RF) coil and others result in a relatively small bore diameter, thus reducing the space available for a patient located in the bore. To alleviate the sensation of claustrophobia, augmented reality goggles (VR goggles) are worn by the patient and used to create a visional impression of a more open feel that will reduce the feeling of anxiety and claustrophobia.

In the case of an extremely confined space around the patient's head, as would be the case, for example, in a PET/MRI environment at high magnetic field (e.g., approximately 7 Tesla), the available space around the head may be limited to a degree where such goggles cannot be donned before the patient enters the bore. Further, in the case of an MR environment, a birdcage type of head coil may be used. Such coils include struts arranged about the patient's head that provide access to the patient's face, thus enabling adjustment of VR goggles by reaching between the struts. However, when conducting a brain study in a PET/MRI environment, access to the patient's face between the struts is not possible due to the confined space in the patient bore.

SUMMARY OF THE INVENTION

A displacement mechanism is disclosed for placing an optical device onto a patient's eyes and removing the optical device from the patient's eyes when the patient is located in a patient bore of a medical imaging system. The mechanism includes a pneumatic device and a resilient element attached between an inner surface of the patient bore and the optical device wherein the resilient element extends through the pneumatic device and wherein the optical device is spaced apart from the patient's eyes in a first position. The mecha- nism also includes a pump that inflates the pneumatic device to move the optical device to a second position wherein the optical device is placed on the patient's eyes wherein inflating the pneumatic device extends the resilient element and biases the resilient element to return to the first position. Further, the mechanism includes a vent valve that vents air from the pneumatic device to return the optical device to the first position. In an embodiment, the pump is actuated by the patient. In addition, the optical device may be virtual reality or augmented reality goggles that display a visional impression of a more open feel that will reduce patient anxiety and a feeling of claustrophobia when located in the patient bore.

In another embodiment, a displacement mechanism is disclosed for placing an optical device onto a patient's eyes and removing the optical device from the patient's eyes when the patient is located in a patient bore of a medical imaging system having a confined head space. The mechanism includes a pneumatic device and a transmit/receive coil located in the patient bore wherein the coil includes a plurality of struts oriented in a longitudinal direction and spaced apart vertically from a patient bed. The mechanism also includes a resilient element attached between an upper strut relative to the patient bed and the optical device wherein the resilient element extends through the pneumatic device and wherein the optical device is spaced apart from the patient's eyes in a first position. In addition, the mechanism includes a pump that inflates the pneumatic device to move the optical device to a second position wherein the optical device is placed on the patient's eyes wherein inflating the pneumatic device extends the resilient element and biases the resilient element to return to the first position. Further, the mechanism includes a vent valve that vents air from the pneumatic device to return the optical device to the first position.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which:

FIG. 4 is a partial side view of a transmit/receive coil configured as a birdcage and depicts an embodiment of the invention wherein the displacement mechanism is attached to a strut of the transmit/receive coil.

DETAILED DESCRIPTION

Figure 1:
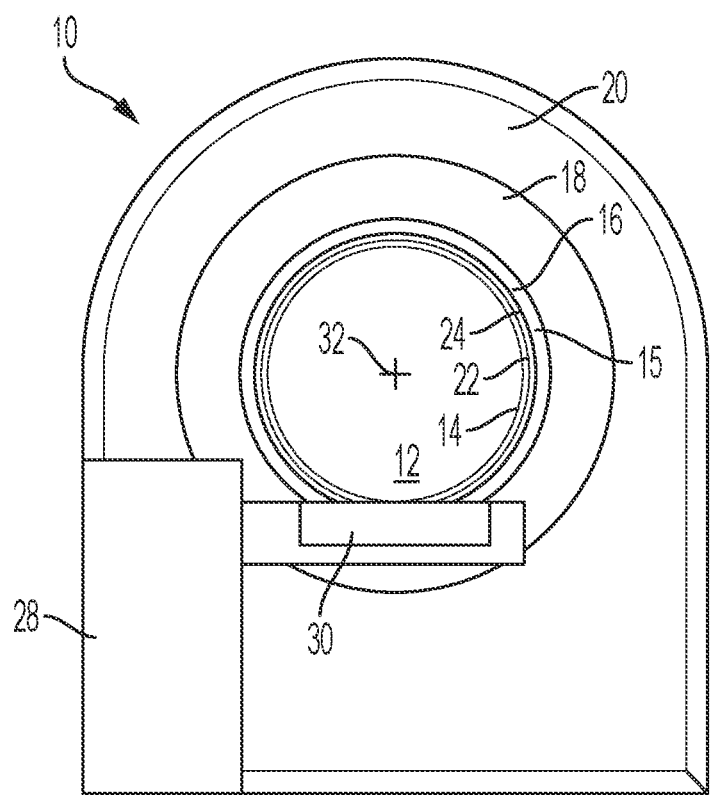
FIG. 1 is a front view of a magnetic resonance/positron emission tomography (MR/PET) imaging system.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

The invention may be used in conjunction with any medical imaging system having a patient bore with a relatively small bore diameter that confines the space around the patient's head such as a magnetic resonance imaging (MR) system, a positron emission tomography (PET) system, a single-photon emission computed tomography (SPECT) system, an X-ray computed tomography (CT) system, a SPECT/CT system and others. For purposes of illustration, the invention will be described in connection with a known MR/PET imaging system.

Referring to FIG. 1, a front view of an MR/PET imaging system 10 is shown. The system 10 includes a patient bore 12 or tunnel that receives a patient to be scanned, RF transmit antenna or body coil 14 (component of the MRI system), PET gantry 16 (part of the PET system) that includes a gantry tube 15, gradient coil 18 (a component of the MRI system) and superconducting magnet 20 (a component of the MRI system). The PET gantry 16 includes a plurality of PET detectors 26 (see FIG. 2) and an RF screen 22 (a component of the MRI system) located on an inner surface 24 of a gantry tube 15. The system 10 further includes a table base 28 having a moveable patient bed 30 for holding a patient. The bed 30 is moveable in a longitudinal direction 35 into and out of the patient bore 12 and substantially parallel to a horizontal or longitudinal axis 32 of the system 10 to enable imaging of the patient by the system 10.

Figure 2:
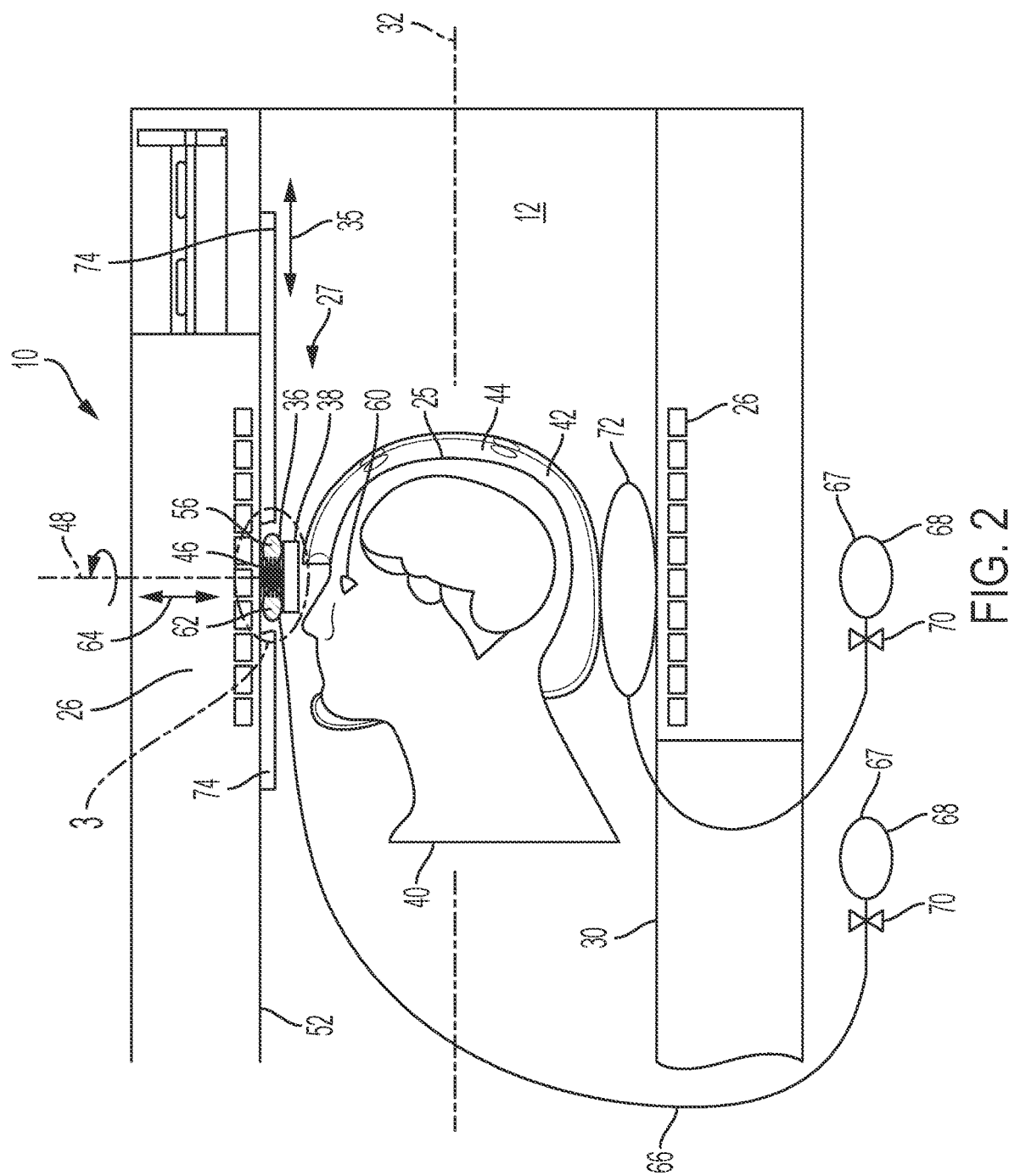
FIG. 2 depicts cross-sectional side views of the MR/PET imaging system and a displacement mechanism that moves an optical device in accordance with the invention.
Figure 3:
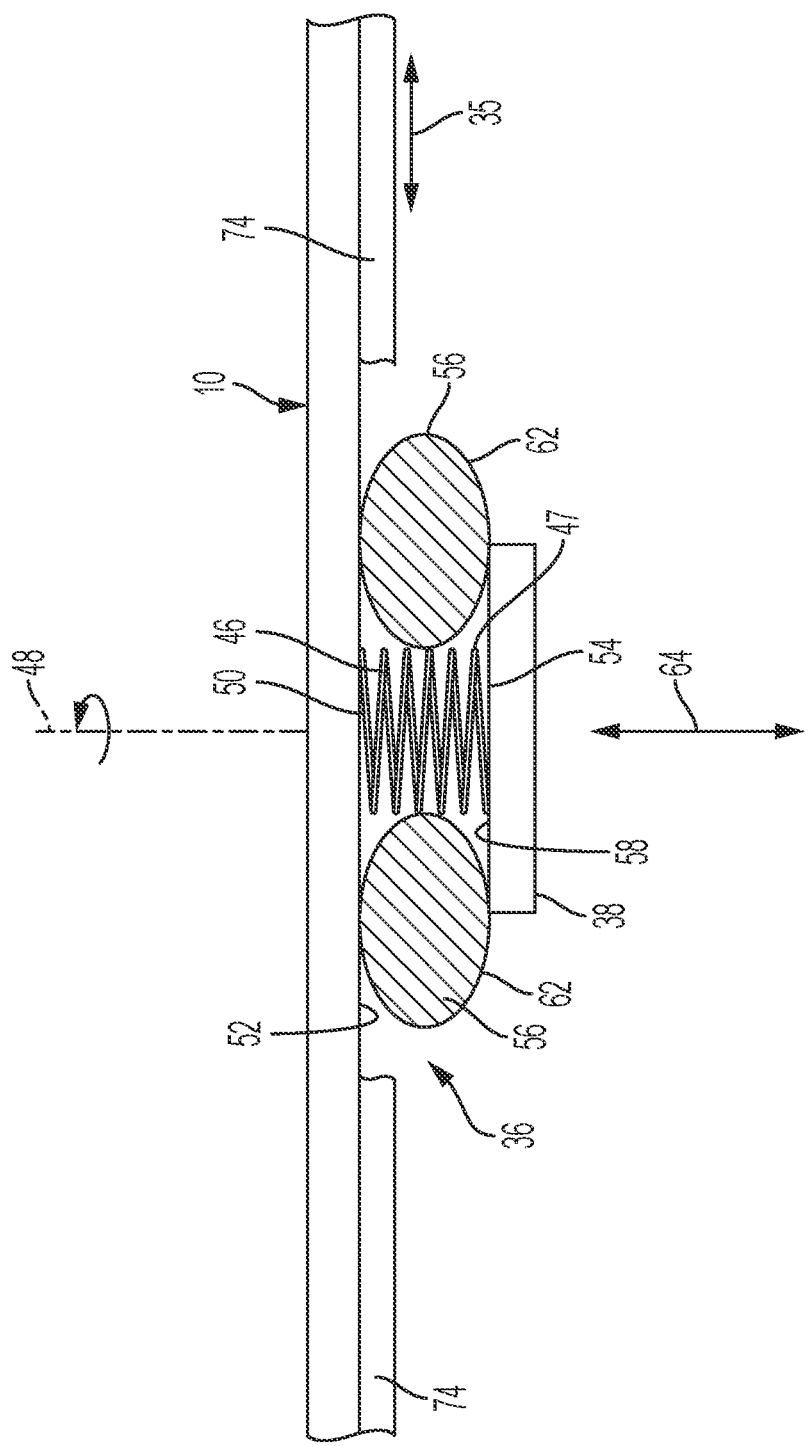
FIG. 3 is an enlarged view of the displacement mechanism and optical device shown in balloon section 3 of FIG. 2.

Referring to FIG. 2, cross-sectional side views are shown of the system 10 and a displacement mechanism 36 that moves an optical device 38 in accordance with the invention. FIG. 3 is an enlarged view of the mechanism 36 and optical device 38 shown in balloon section 3 of FIG. 2. Referring to FIGS. 2 and 3, the mechanism 36 serves to displace or move the optical device 38 toward, and away from, a patient 40 or test subject lying in a supine position in the patient bore 12. When conducting a brain study, the patient 40 wears a transmit/receive coil 42 that is part of the MR system. The transmit/receive coil 42 may be configured as an open face helmet 44 as shown in FIG. 2 or as a birdcage 76 as shown in FIG. 4.

In accordance with an aspect of the invention, the mechanism 36 includes at least one resilient element 46 aligned with a vertical axis 48 of the system 10. The resilient element 46 extends downwardly into the patient bore 12. The resilient element 46 includes a first or attachment end 50 that is attached to an inner surface 52 of the patient bore 12 and a second or free end 54 that is attached to a top surface 58 the optical device 38. The resilient element 46 extends through at least one passive pneumatic device 56 located between the inner surface 52 of the patient bore 12 and the top surface 58. In a first position, the optical device 38 is spaced apart from the patient's eyes 60 and the resilient element 46 has a first size. In accordance with an aspect of the invention, the mechanism 36 is fabricated from materials that are MR compatible and made of low density materials to minimize PET attenuation.

The resilient element 46 may be, for example, a spring such as a helical spring 47 or other type of spring fabricated from a non-metallic material such as plastic. Alternatively, the resilient element 46 may be a compliant spring mechanism fabricated using additive manufacturing techniques wherein a spring characteristic is generated through deformation of a section of a continuous plastic structure that is thinner than another section. In another embodiment, first and second opposing air bladders may be used as the resilient element 46. In this configuration, a first bladder remains inflated whereas a second bladder is inflated and deforms or overcomes the first bladder to form a resilient element.

The optical device 38 may be a device that displays video such as virtual reality goggles, augmented reality goggles, wearable computer glasses or other optical devices. The optical device 38 is used to create a visional impression of a more open feel that will reduce the feeling of anxiety and claustrophobia. In addition, the optical device 38 may also be used as a mechanism for stimulating the brain for research purposes.

The pneumatic device 56 may include a first air bladder 62 that extends circumferentially around the resilient element 46 to form a collar around the resilient element 46. In use, the first bladder 62 is inflated which causes a size of the first bladder 62 between the inner surface 52 and the top surface 58 to expand or increase. Inflation of the first bladder 62 in turn increases a first size of the resilient element 46, thus biasing the resilient element 46 to return to the first size, and causes downward movement 64 of the optical device 38 toward the patient's face. The first bladder 62 is inflated until the optical device 38 is moved to a second position wherein the optical device 38 is placed on the patient's eyes 60, thus enabling the patient 40 to view images or video displayed by the optical device 38. When a scanning or imaging procedure is complete, air is vented from the inflated first bladder 62. This decreases the size of the first bladder 62 and causes the resilient element 46 to return to the first size, thus removing the optical device 38 from the patient's face and returning the optical device 38 to the first position to alleviate any sensation of claustrophobia felt by the patient 40 due to placement of the optical device 38 on the patient's face.

In accordance with an aspect of the invention, the mechanism 36 may be preinstalled in the patient bore 12 before the patient 40 is moved into the patient bore 12. This enables use of the optical device 38 in a patient bore 12 of an imaging system having a relatively small bore diameter wherein the space around the patient's head 25 is confined and the optical device 38 cannot be donned before the patient enters the patient bore 12. Such a confined space 27 may be imposing or intimidating to those that are either young or for adults who suffer from claustrophobia or other conditions. The optical device 38 is used to create a visional impression of a more open feel that will reduce the feeling of anxiety and claustrophobia.

To alleviate a potential sensation of claustrophobia when lowering the optical device 38 onto the patient's face, inflation of the first bladder 62 may be controlled by the patient 40. In an embodiment, the first bladder 62 is connected via a tube 66 to a pump 67 such as a bulb pump 68 used to force air into the first bladder 62 and inflate the first bladder 62. In use, the patient 40 actuates or squeezes and releases the bulb pump 68 at a desired amount and rate sufficient to lower the optical device 38 onto the patient's eyes 60 at a desired speed such that the patient 40 is comfortable and does not have a sensation of claustrophobia. Since the patient 40 operates the bulb pump 68, the patient 40 is in control of the process and the risk of a panic reaction is reduced.

The mechanism 36 further includes a vent valve or dump valve 70 in fluid communication with the tube 66. If the patient 40 is anxious and wishes to alleviate anxiety while in the patient bore 12, the valve 70 may be opened by the patient 40 to vent air from the first bladder 62 to cause an emergency release of air that quickly deflates the first bladder 62, thus quickly removing the optical device 38 from the patient's face and returning the optical device 38 to the first position wherein the optical device 38 is spaced apart from the patient's eyes 60 as previously described. The emergency release of air may be detected by sensors and reported to an operator of the system 10 (e.g., by an audio/visual alarm, console message, etc.). In addition, an emergency release of air may be initiated by either a clinician or an operator of the system 10.

In another embodiment, the mechanism 36 is controlled by an operator of the system 10 who receives patient feedback through, for example, verbal communication from the patient 40. In addition, the optical device 38 may have video capture features (e.g., used for eye tracking) and the video material could be analyzed during the donning of the optical device 38 to determine the fit and comfort of the patient 40. The video material could further be analyzed during the course of research to detect a state of anxiety by observing pupil dilation or similar hallmarks of anxiety.

In yet another embodiment, a second air bladder 72 may be positioned under the patient's head 25. The second air bladder 72 may be inflated by the patient 40 to raise the patient's head 25 and move the patient's eyes 60 toward the optical device 38 to assist in positioning of the patient's eyes 60 relative to the optical device 38. In addition, the resilient element 46 may be moveably attached to a channel or guide element 74 (partially shown in FIG. 2) attached to the inner surface 52. The guide element 74 enables movement of the resilient element 46 in the longitudinal direction 35 to enable fine adjustments when aligning the optical device 38 with a patient's eyes 60. Further, the resilient element 46 may be rotatably attached to the inner surface 52 to enable rotation of the optical device 38 about the vertical axis 48 to adjust for a patient 40 that is on their side, slightly rolled to the side or if their head 25 is tilted.

Referring to FIG. 4, a partial side view of a transmit/receive coil 42 when configured as a birdcage 76 is shown and depicts an embodiment of the invention wherein the mechanism 36 is attached to a strut of the transmit/receive coil 42. In particular, the transmit/receive coil 42 is located on the patient bed 30 and includes a substantially cylindrically shaped enclosure 78 for receiving the patient's head 25. The enclosure 78 includes a plurality of struts 80 that are oriented in the longitudinal direction 35 about the patient's head 25 and spaced apart vertically relative to the bed to form an enclosure 78 having a partially open configuration. In an embodiment, the enclosure 78 may include first 82, second 84, third 86 and fourth 88 struts each located progressively further from the bed 30, respectively, wherein the second strut 84 is located further from the bed 30 than the first strut 82, the third strut 86 is located further from the bed 30 than the second strut 84 and the fourth strut 88 is located further from the bed 30 than the third strut 86. In an embodiment, the resilient element 46 is attached to an upper strut such as the fourth strut 88 (i.e., the strut furthest from the bed 30 in the vertical direction) or other struts that are suitable for attachment of the resilient element based on, for example, access to the patient's eyes.

In the embodiment shown in FIG. 4, the resilient element 46 is attached to the fourth strut 88 instead of the inner surface 52 of the patient bore 12 as shown in FIGS. 2 and 3. This forms an arrangement wherein the mechanism 36 is located between the fourth strut 88 and the optical device 38. The mechanism 36 may then be operated as previously described to enable movement of the optical device 38 toward the patient 40 for placement on the patient's eyes 60 and movement of the optical device 38 away from the patient 40. In particular, the first bladder 62 is inflated which causes a size of the first bladder 62 between the fourth strut 88 and the top surface 58 to increase. Inflation of the first bladder 62 in turn increases a first size of the resilient element 46, thus biasing the resilient element 46 to return to the first size, and causes downward movement 64 of the optical device 38 toward the patient's face. The first bladder 62 is inflated until the optical device 38 is moved to a second position wherein the optical device 38 is placed on the patient's eyes 60, thus enabling the patient 40 to view images or video displayed by the optical device 38. When a scanning or imaging procedure is complete, air is vented from the inflated first bladder 62. This decreases the size of the first bladder 62 and causes the resilient element 46 to return to the first size, thus removing the optical device 38 from the patient's face and returning the optical device 38 to the first position to alleviate any sensation of claustrophobia felt by the patient 40 due to placement of the optical device 38 on the patient's face.

The invention substantially improves patient comfort for an imaging system that is space constrained. In addition, allowing the patient to be in control of placement, and removal of, the optical device will reassure the patient and reduce overall anxiety. This will increase success of research studies and can reduce cross-effects on outcome of studies.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A displacement mechanism for placing an optical device onto a patient's eyes and removing the optical device from the patient's eyes when the patient is moved into a patient bore of a medical imaging system by a patient bed wherein the patient's head is oriented in a horizontal position in the patient bore, comprising:
   a pneumatic device that extends in a downward direction toward the patient when the pneumatic device is inflated;
   a resilient element attached between a top surface of the patient bore and the optical device wherein the resilient element extends downward from the top surface and through the pneumatic device wherein the optical device is suspended from the top surface and spaced apart from the patient's eyes in a first position and wherein the patient bore forms a confined space around the patient's head;
   further including a guide element attached to the top surface of the bore to enable movement of the resilient element and optical device in a longitudinal direction corresponding to a longitudinal axis of the system;
   a pump that inflates the pneumatic device in a downward direction to move the optical device downward to a second position wherein the optical device is placed on the patient's eyes when the patient is moved into the patient bore and the patient's head is oriented in the horizontal position and wherein inflating the pneumatic device extends the resilient element and biases the resilient element to return to the first position and wherein the pneumatic device, resilient element and optical device are preinstalled in the patient bore before the patient is moved into the patient bore; and a vent valve that vents the pneumatic device to deflate the pneumatic device wherein upon deflation of the pneumatic device the bias of the resilient element causes upward movement of the optical device to return the optical device to the first position.

2. The mechanism according to claim 1, wherein the pump is actuated by the patient.

3. The mechanism according to claim 1, wherein the pneumatic device includes an inflatable air bladder.

4. The mechanism according to claim 1, wherein the resilient element is a helical spring.

5. The mechanism according to claim 1, wherein the vent valve may be actuated by either the patient or a clinician.

6. The mechanism according to claim 1, further including an inflatable bladder located under the patient's head to move the patient's eyes toward the optical device when the bladder is inflated.

7. A displacement mechanism for placing an optical device onto a patient's eyes and removing the optical device from the patient's eyes when the patient is moved into a patient bore of a medical imaging system by a patient bed having a confined head space wherein the patient's head is oriented in a horizontal position in the patient bore, comprising:

a pneumatic device that extends in a downward direction toward the patient when the pneumatic device is inflated;

a transmit/receive coil located in the patient bore wherein the coil includes a plurality of struts oriented in a longitudinal direction and spaced apart vertically from a patient bed;

a resilient element attached between a top strut relative to the patient bed and the optical device wherein the resilient element extends downward from the top strut and through the pneumatic device and wherein the optical device is suspended from the top strut and spaced apart from the patient's eyes in a first position;

further including a guide element attached to the top surface of the bore to enable movement of the resilient element and optical device in a longitudinal direction corresponding to a longitudinal axis of the system;

a pump that inflates the pneumatic device in a downward direction to move the optical device downward to a second position wherein the optical device is placed on the patient's eyes when the patient is moved into the patient bore and the patient's head is oriented in the horizontal position and wherein inflating the pneumatic device extends the resilient element and biases the resilient element to return to the first position and wherein the pneumatic device, resilient element and optical device are preinstalled on the top strut before the patient is moved into the patient bore; and a vent valve that vents the pneumatic device to deflate the pneumatic device wherein upon deflation of the pneumatic device the bias of the resilient element causes upward movement of the optical device to return the optical device to the first position.

8. The mechanism according to claim 7, wherein the pump is actuated by the patient.

9. The mechanism according to claim 7, wherein the pneumatic device includes an inflatable air bladder.

10. The mechanism according to claim 7, wherein the resilient element is a helical spring.

11. The mechanism according to claim 7, wherein the vent valve may be actuated by either the patient or a clinician.

12. The mechanism according to claim 7, further including an inflatable bladder located under the patient's head to move the patient's eyes toward the optical device when the bladder is inflated.

13. The mechanism according to claim 7, wherein the system is a magnetic resonance/positron emission tomography (MR/PET) imaging system.

* * * * *